United States Patent
Fuller

(10) Patent No.: US 7,505,561 B1
(45) Date of Patent: Mar. 17, 2009

(54) SCHLIEREN-TYPE RADIOGRAPHY USING A LINE SOURCE AND FOCUSING OPTICS

(76) Inventor: Michael Keith Fuller, 22703 Manolete Dr., Salinas, CA (US) 93908

( * ) Notice: Subject to any disclaimer, the term of this patent is extended or adjusted under 35 U.S.C. 154(b) by 0 days.

(21) Appl. No.: 11/985,649

(22) Filed: Nov. 17, 2007

(51) Int. Cl.
  *G01N 23/201* (2006.01)
  *G01N 23/20* (2006.01)
(52) U.S. Cl. .............................. 378/86; 378/70; 378/87
(58) Field of Classification Search ............. 378/4, 378/6, 7, 19, 70, 86–90, 84, 79, 208
  See application file for complete search history.

(56) References Cited

U.S. PATENT DOCUMENTS

| | | | |
|---|---|---|---|
| 5,245,648 A * | 9/1993 | Kinney et al. | 378/43 |
| 7,409,042 B2 * | 8/2008 | Bertozzi et al. | 378/88 |
| 2008/0181363 A1 * | 7/2008 | Fenter et al. | 378/70 |

* cited by examiner

Primary Examiner—Irakli Kiknadze

(57) ABSTRACT

A system for observing the internal features of an object, such that the object's internal absorption, refraction, reflection and/or scattering properties are visualized, is disclosed. An embodiment may include one or more beams of penetrating radiation, an object with internal features to be imaged, a single or an array of radiation optics, and a detection system for capturing the resultant shadowgraph images. The beam(s) of radiation transmitted through the object typically originate from a line-shaped source(s), which has high spatial purity along the narrow axis, and low spatial purity in the perpendicular, long axis. In the long axis, radiation optic(s) capture and focus diverging rays exiting from the object to form a high resolution image of the object, without which optic(s) the shadowgraph would have blurring in this axis. Such shadowgraph is naturally well defined in the opposite axis of narrow beam origin and can reveal an object's refraction, reflection and/or scattering properties along that axis. An embodiment may also include discriminators (stops, phase shifters, analyzer crystals, etc.) in the beam exiting the object. An embodiment may also include mechanisms for scanning whereby a two-dimensional or three-dimensional image of a large object is made possible. An embodiment may also include an image of an object's internal features being derived from an analysis of the radiation and/or radiation waveform exiting the object.

19 Claims, 15 Drawing Sheets

SCHLIEREN-TYPE RADIOGRAPHY USING A LINE SOURCE AND FOCUSING OPTICS

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

This invention relates to a method for detecting an image of the internal features of an object, such as one mass internal with respect to another mass wherein the one mass has a refraction content, reflection content and/or scattering content different than the other mass, in particular, of materials where mass radiation absorption contrast is less significant. This non-provisional application is a continuation of provisional application 60/860,023 from which priority is claimed.

REFERENCES

U.S. Pat. No. 5,319,694 June 1994 Ingaletal.
U.S. Pat. No. 5,406,609 April 1995 Arai et al.
U.S. Pat. No. 5,428,657 June 1995 Papanicolopoulos et al.
U.S. Pat. No. 5,457,726 October 1995 Miyazaki
U.S. Pat. No. 5,457,727 October 1995 Frijlink
U.S. Pat. No. 5,579,363 November 1996 Ingal et al.
U.S. Pat. No. 5,715,291 February 1998 Momose
U.S. Pat. No. 5,717,733 February 1998 Kurbatov et al.
U.S. Pat. No. 5,787,146 July 1998 Giebeler
U.S. Pat. No. 5,802,137 September 1998 Wilkins
U.S. Pat. No. 5,805,662 September 1998 Kurbatov et al.
U.S. Pat. No. 5,850,425 December 1998 Wilkins
U.S. Pat. No. 5,923,720 July 1999 Barton et al.
U.S. Pat. No. 5,949,847 September 1999 Terada et al.
U.S. Pat. No. 5,987,095 November 1999 Chapman et al.
U.S. Pat. No. 6,018,564 January 2000 Wilkins
U.S. Pat. No. 6,035,227 March 2000 Shmueli
U.S. Pat. No. 6,038,285 March 2000 Zhong et al.
U.S. Pat. No. 6,212,254 April 2001 Wilkins
U.S. Pat. No. 6,269,144 July 2001 Dube et al.
U.S. Pat. No. 6,385,289 May 2002 Kikuchi
U.S. Pat. No. 6,493,422 December 2002 Wilkins et al.
U.S. Pat. No. 6,567,496 May 2003 Sychev
U.S. Pat. No. 6,577,708 June 2003 Chapman et al.
U.S. Pat. No. 6,594,335 July 2003 Davidson
U.S. Pat. No. 6,804,324 October 2004 Martynov et al.
U.S. Pat. No. 6,870,896 March 2005 Protopopov
U.S. Pat. No. 6,947,521 Chapman et al.
U.S. Pat. No. 7,062,015 June 2006 Lewis
U.S. Pat. No. 7,076,025 Chapman et al.
U.S. Pat. No. 7,107,693 Nesch et al.
U.S. Pat. No. 7,280,636 Nesch et al.
2002/0027970 March 2002 Chapman
2004/0196957 October 2004 Ando
2004/0258202 December 2004 Wernick
2005/0117705 June 2005 Morrison
2005/0129169 June 2005 Donnelly
2005/0259788 November 2005 Hasnah
2006/0039532 February 2006 Wu
2006/0235296 October 2006 Mattiuzzi
2006/0072702 April 2006 Chapman

FOREIGN PATENT DOCUMENTS

95/05725 February, 1995 WO

OTHER REFERENCES

D Chapman, W. Thomlinson, R. E. Johnson, D. Washbum, E. Pisano. N. Gmur, Z. Zhong, R. Menk, F. Arfelli and D. Sayers, X-Ray Refraction Imaging (XRI) Applied to Mammography, published Oct. 31, 1997. cited by other.
V. N. Ingal and E. A. Beliaevskaya, Phase Dispersion Introscopy, (published prior to Oct. 16, 1996). cited by other.
V. N. Ingal and E. A. Beliaevskaya, X-ray plane-wave topography observation of the phase contrast from a non-crystalline object, J. Phys. D: Appl. Phys. 28 (1995) 2314-2317. cited by other.
V. N. Ingal and E. A. Belyaevskaya, Method of phase-dispersion introscopy, Tech. Phys. 42 (1), January 1997. cited by other.
V. N. Ingal and E. A. Beliaevskaya, Phase dispersion radiography of biological objects, Physica Medica. vol. X11, No. 2, April-June 1996. cited by other.
V. A. Bushuev, V. N. Ingal and E. A. Belyaevskaya, Dynamical Theory of Images Generated by Noncrystalline Objects for the Method of Phase-Dispersive Introscopy, Crystallography Reports, vol. 41, No. 5, 1996, pp. 766-774. cited by other.
V. A. Bushuev, E. A. Beliaevskaya and V. N. Ingal, Wave-optical description of X-ray phase contrast images of weakly absorbing non-crystalline objects, II Nuovo Cimento, vol. 19D, No. 2-4, February-April 1997. cited by other.
V. N. Ingal and E. A. Beliaevskaya, Imaging of biological objects in the plane-wave diffraction scheme, II Nuovo Cimento, vol. 19D, No. 2-4, February-April 1997. cited by other.
V. N. Ingal and E. A. Beliaevskaya, Phase Dispersion Introscopy, Surface Investigation, vol. 12, pp. 441-450, 1997. cited by other.
Tetsuya Ishikawa, Selshi Kikuta and Kazutaka Kohra, Angle-Resolved Plane Wave X-Ray Topography, Japanese Journal of Applied Physics, vol. 24, No. 7, July 1985, pp. L559-L562. cited by other.
Hasnah et al.: Diffraction Enhanced Imaging Contrast Mechanisms in Breast Cancer Specimens, Medical Physics 29, pp. 2216-2221, 2002. cited by other.

PRIOR ART

Radiography has been used in medical imaging and for non-destructive testing, and in computed tomography. Traditional medical radiographic imaging is based upon the difference between photoelectric absorption of x-rays between soft-tissue and bones or contrast media. Traditional radiography is less useful to distinguish differences between different materials, such as healthy and diseased human tissues, or flaws in manufactured products. At high energies utilized to image deep body anatomy, the image contrast of soft-tissues due to absorption decreases markedly.

Compared to traditional x-ray absorption radiography, schlieren phase radiography is better suited for visualizing soft-tissue structures which do not appreciably absorb x-rays, but which may contain non-absorptive structural details. Internal structures may produce a measurable deviation in the direction and velocity of the incident radiation because of local variations in the refractive index, and variations in density and thickness of those structures. Phase disturbances occur at interfaces between soft-tissue planes that have slightly different refractive indices and thicknesses. Within soft-tissues, incident radiation is refracted by spatially oriented molecular and atomic planes, thereby experiencing a significant shift in phase, corresponding to a change in direction.

Technological improvements in spectral and spatial filtering, particularly the availability of large perfect crystals, have allowed for several prior methods of performing schlieren phase radiography. Outside of a few special cases (see E. Förster et al, 1980), these previous methods have been confined to synchrotron source facilities, which can provide an x-radiation beam with the appropriate spatial and spectral characteristics and at a sufficient flux for some applications. These prior schlieren radiography methods have become known to skilled users and are alternatively called phase contrast imaging, diffraction enhanced imaging, dark field radiography, multiple image radiography and other terms.

Generally, there are five established types of schlieren phase radiography, involving either: 1) using direct in-line geometry, 2) use of an analyzer crystal or structured multilayer analyzer after the object, 3) phase derivation from at least two distinct projection images, 4) holographic interferometry, and 5) Talbot interferometry. These prior methods produce either an analog image or employ mathematical processing of detected intensity information to derive a digital image. All of these methods require a synchrotron radiation source, where high spatial purity in one or both axes is the result of the generating technology (i.e. bending magnet, wiggler, etc.) and the extreme distance from origin to object, for performing medical imaging.

Of these schlieren radiography types, several sub-types have been proposed for using a diffractive analyzer crystal placed after the object. The analyzer surface is geometrically aligned within the incident beam, to be more-or-less parallel to the incident beam. Because of this specific analyzer-beam geometry and also because of the crystal's uniformly oriented diffraction planes, the analyzer crystal possesses a rocking curve which is sensitive to microradian alterations in the direction of the incident beam, which are induced by changes in the refractive index within soft-tissues. Thus, depending on the orientation of the crystal to the incident beam of coherent x-rays, the analyzer crystal can select for either the schlieren image (from the refracted/deflected beam) or the absorption image (from the direct beam). Moreover, in both cases of absorption and of refraction, the analyzer crystal is used simultaneously as a Compton scatter reduction optic. Two images from the opposite sides of the analyzer crystal's rocking curve can be combined on a pixel-by-pixel basis to obtain images that contains either refraction or absorption information. This technique has proven useful for research purposes with synchrotron sources. However, the reduction of radiation flux from beam-conditioning monochromators renders the techniques unsuitable for use with conventional laboratory x-radiation sources.

Ingal et al., U.S. Pat. Nos. 5,319,694, 5,579,363 discloses methods for obtaining an x-ray phase image where the phase information is only for one axis in the two-dimensional image. Collimated radiation is transmitted through an object and diffracted through a Laue type crystal analyzer. While deflecting the crystal analyzer interferogram images of the internal structure of the object are monitored and a position of the crystal analyzer which provides an image with maximum contrast is selected. The diffracted beam emerging from the crystal analyzer carries information on phase attributes of the internal structure of the object. Because of the significant radiation flux required, Ingal's method is also limited to non-conventional synchrotron sources for a few medical imaging applications.

Chapman et al, U.S. Pat. Nos. 5,987,095, 6,577,708, 6,947,521, 7,076,025 discloses an improvement over Ingal's approach in that two detected images are captured and then are subtracted to eliminate absorption effects. This method presets the analyzer crystal positions, which improves on Ingal's approach. However, no change in the required flux is available under Chapman and those methods require use of a synchrotron source for medical applications.

Similarly, the use of structured multilayer reflectors in place of the crystal analyzer, as proposed by Protopopov U.S. Pat. No. 6,870,896 and Martynov U.S. Pat. No. 6,804,324, do not mitigate the demand for source intensity and are limited to synchrotron sources.

Wilkens et al, U.S. Pat. Nos. 6,018,564, 6,212,254, 6,226,353, 6,493,422 discloses methods for enhancing the edges of density boundaries from overlapping rays originating from microfocus sources and transmitted through an object. This phase radiography technique uses natural interference of these overlapping rays in the resultant image. Wilkins's approach uses a good spatial purity in the rays from the source, and an extended distance between the object and the detector. Because microfocus sources are inherently low power, and the flux at the detector is subject to reduced intensity by the square of distance from the source, this approach is limited to long exposure applications and not useful for most medical imaging.

At least one method has been presented for using higher flux conventional line-focus x-ray sources. Chapman, patent application, U.S. 2004/957884, discloses a method using a line source of radiation. In this method, non-matching monochromator crystals are used to condition the output beam of a commercial line source. However, the greater available initial flux is only partially useful and thus of limited benefit to the schlieren radiography arrangement.

There is an apparent need for a schlieren phase radiological system that can be used for medical imaging to detect smaller and earlier stages of cancer and other diseases, and small flaws in non-biological objects, using conventional laboratory radiation sources, which are useable in a clinical setting.

BRIEF SUMMARY OF INVENTION

It is an object of this invention to provide a system suitable for medical schlieren phase radiography using laboratory x-radiation sources. In the context of this specification, radiation is said to mean x-rays, electrons, neutrons, extreme ultraviolet light or other forms of penetrating energy. The present invention provides a schlieren radiography system which is capable of observing the absorption, refraction, reflection and/or scattering properties of the internal features of an object. The present invention further provides a system readily to form a reconstructed phase image of an object and a computed tomogram of an object. The present invention also provides an imaging system which is able to generate a dual energy subtraction phase image, selective scatter image, and magnetically induced birefringence image. The present invention achieves the above accomplishments with novel uses of line origin radiation sources and novel uses of radiation focusing optics.

This invention uses powerful line focus radiation sources, such as conventional line origin x-ray tubes, to perform schlieren phase radiography. Line origin x-ray tubes operate at much higher power than spot origin tubes as the tube current is distributed over a larger surface area of the anode. A line origin x-ray tube typically has the narrow width of the projected origin at 30-microns and the length at 10-mm, and can operate at tube power as high as 3,000 watts—about 100 times greater than an x-ray tube with a 30-micron round spot origin. Such sources are commercially available in a variety of target materials, each of which has a unique output spectrum. An alternative source of radiation useful for this invention would be a moderated neutron source where slits are used to provide thermal or cold neutrons beams with high spatial purity in one axis. This invention is also useful with a synchrotron source.

Prior to this invention, line-origin x-ray tubes have not been used for imaging because in line mode, one axis of the resultant shadowgraph would be blurred. This invention overcomes blurring in the long axis of radiation origin by use of a focusing element to optically construct an image in that axis. A focusing element useful for this invention is a Compound Refractive Lens (CRL). Several unique CRL lens designs exist for one-dimensional focusing. Most commonly, a 1-D lens is formed by a linear series of holes formed in some medium each placed in close proximity to the next. The bi-concave surfaces between any two holes acts as a single focusing lens for x-ray wavelengths. Of course, two one-dimensional CRL's when crossed at ninety degrees form a 2-D lens assembly. In addition to crossed 1-D lenses, there are several available designs for 2-D CRL units. Various compound refractive lens designs, curved crystal sets, multilayer mirrors, or other focusing optics are also suitable for constructing an image of the object in the long axis of radiation line origin.

Phase-shifts experienced by an incident ray can be observed as a microradian deflection only when employing a coherent beam (with almost no transverse beam divergence) of incident radiation to illuminate the object under investigation. Coherent light can be considered as a train of parallel, unperturbed planar wavefronts, propagating along—and perpendicular to the optical axis. Good spatial purity can also be in the form of spherical or cylindrical wavefronts. Such coherence can be found in small point origins observed at large distances, and thus are coherent in both vertical and horizontal axes. High coherence is also achieved by standard sources and the use of asymmetric crystal monochromators, which provide coherence in only one axis. These crystals have the attribute of receiving incident rays of higher divergence and reflecting rays of lower divergence, albeit at the cost of intensity as the beam is expanded in the axis of diffraction. As described above, prior schlieren radiography techniques have proven the validity of using radiation beams that are coherent in only one axis.

After the incident wavefront interacts with the constituent structures of the object, a warping is produced in the formerly perfect waveform. The incident waveforms are converted in the object into a three-dimensionally distorted wavefront, which possesses a phase-shifted profile. Refractive disturbances are maximal at interfaces of different densities within the object that are oriented parallel to the beam direction. Only in a direction parallel to the incident beam, do the edges of differing density components possess maximum physical thickness relative to the beam direction. Thus, to acquire the highest quality schlieren image, only tissue interfaces that are oriented parallel to the incident beam can measurably deviate a spatially pure incident ray.

In schlieren phase radiography, the spatial quality needed in the illuminating radiation depends on the type of object to be imaged. The discussed medical imaging application (where refractive deviations at the boundaries of cancerous lesions are very slight) requires low divergence in at least one axis of the illuminating radiation beam. By inclusion of radiation optical components, and particularly a line-focus radiation source and radiation imaging optics, this invention makes possible novel arrangements of schlieren radiography—in that good beam quality in provided in the narrow axis of radiation line origin and blurring is not allowed in the long axis of radiation line origin.

BRIEF DESCRIPTION OF THE SEVERAL VIEWS OF THE DRAWING

The invention will be further described, by way of example only, with reference to the accompanying drawings, in which.

DETAILED DESCRIPTION OF THE INVENTION

Figure 1:
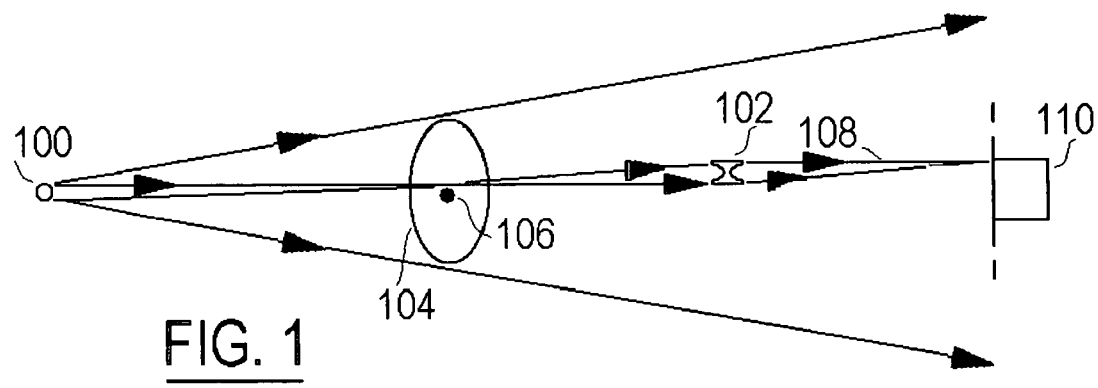
FIG. 1 is a diagrammatic plan top view of a schlieren radiography system in accordance with an embodiment of the invention, wherein phase and/or scattering content is represented entirely in one axis of the image.

A diagrammatic top view of a system for forming an image of an object in accordance with an embodiment of this invention is shown in FIG. 1. A radiation line origin with an axis of narrow spatial dimension 100 produces rays of high spatial purity. Some of these rays transmit through the object 104. A subset of these rays will transmit the boundary of components of differing density 106 and fall incident onto a two-dimensional focusing optic 102. Rays 108 deviated by the refractive properties of said boundary will be brought to focus on a detector 110. Rays from nearby regions that were not deviated will also be focused on the detector 110. The two sets of rays thus interfere and produce contrast enhancement of the image of said boundary of differing densities.

Figure 2:
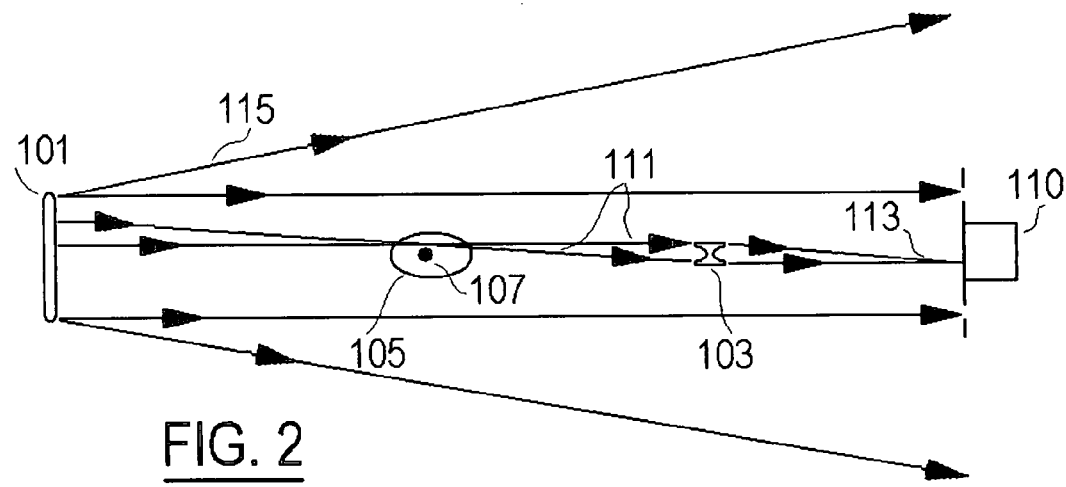
FIG. 2 is a diagrammatic plan side view of the system described in FIG. 1, wherein a radiation optic captures and focuses points within the object in high resolution.

A diagrammatic side view of the same system is shown in FIG. 2. A radiation line origin with an axis of long spatial dimension 101 produces rays of low spatial purity 115. No rays in this axis are expected to interfere and produce contrast enhancement. Instead, rays emitted from any point in the object 105 will fill the aperture of the two-dimensional focusing optic 103 and be brought to focus on a detector 110. Consequently, rays within the field of view of the radiation focusing optic 111 that transmit through the object 105 and the previously discussed boundary of components of differing density 107 will also be focused 113 on the detector. This optical condition results in improved resolution as the long axis of radiation origin 101 backlights all features within the object 105.

The resulting image produced by this system has particularly high resolution in one axis with edge enhancement of certain features in the other axis. The diagrammatic views of FIG. 1 and FIG. 2, and other figures herein described, show the radiation focusing optic as a single refractive lens. Because the index of refraction for radiation in most materials is less than 1, the shape of the lens is biconcave. In practice, the refraction is very slight for a single lens and a series of lenses are needed to produce a useful focal length. Such designs are known as compound refractive lenses (CRL's) and are herein represented as a single lens element for instructive purposes. An array of such CRL's with an accompanying array of detectors would increase the field of view. A total image would be the result of electronically stitching the arrayed images together. Scanning would result in full 2-D or 3-D image sets. A practitioner skilled in the art could also employ other radiation focusing optics to equal effect.

Figure 3:
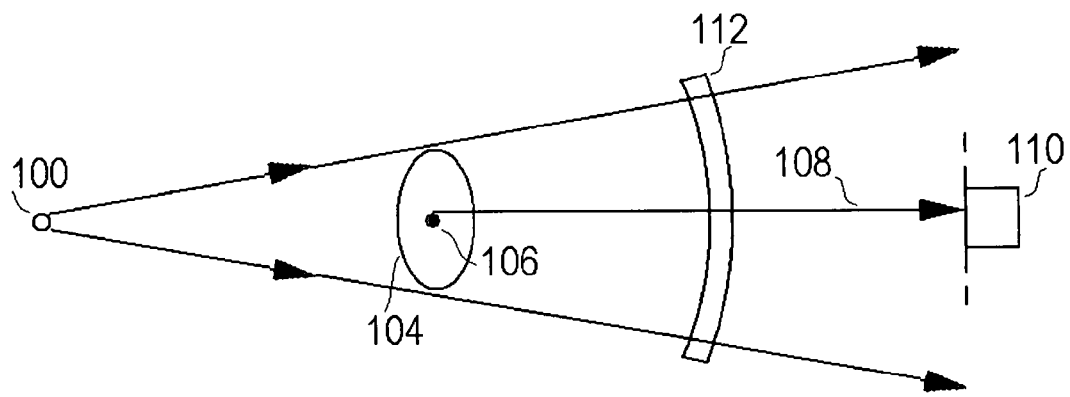
FIG. 3 is a diagrammatic plan top view of a schlieren radiography system in accordance with an embodiment of the invention, wherein phase and/or scattering content is represented entirely in one axis of the image in a wide field of view.

A diagrammatic top view of a system for forming an image of an object in accordance with an embodiment of this invention is shown in FIG. 3. A radiation line origin with an axis of narrow spatial dimension 100 produces rays of high spatial purity. Some of these rays transmit through the object 104. A subset of these rays will transmit the boundary of components of differing density 106 and also transmit a one-dimensional focusing optic 112. The focusing optic 112 is here diagramed as having a uniform curvature such that rays in this axis are transmitted without displacement and without being focused. Rays deviated by the refractive properties of this boundary 108 will fall incident on a detector 110. Rays from nearby regions that were not deviated will also fall on the detector 110. Provided that adequate distance to the detector allows for a difference in path lengths of a wavelength, these two sets of rays will interfere, providing contrast enhancement in the image of the boundary of differing densities.

Figure 4:
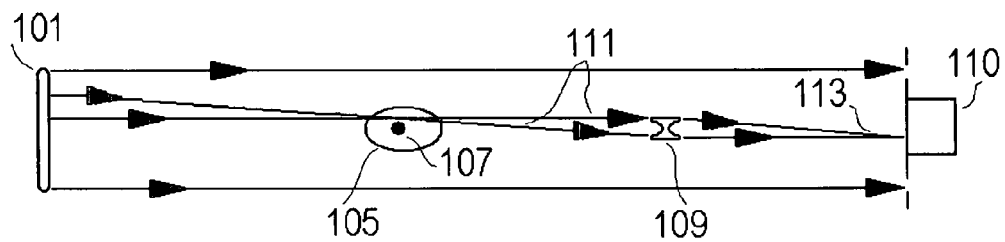
FIG. 4 is a diagrammatic plan side view of the system described in FIG. 3, wherein a one-dimensional radiation optic captures and focuses points within the object over a large field of view.

A diagrammatic side view of the same system is shown in FIG. 4. A radiation line origin with an axis of long spatial dimension 101 produces rays of low spatial purity. No rays in this axis are expected to interfere and produce contrast enhancement. Instead, rays emitted from any point in the object 105 will fill the aperture of the one-dimensional focusing optic 109 and be brought to focus on a detector 110. Consequently, rays within the field of view of the radiation focusing optic 111 that transmit through the object 105 and the previously discussed boundary of components of differing density 107 will also be focused on the detector 113. This optical condition results in improved resolution as the long axis of radiation origin 101 backlights all features within the object 105.

The resulting image produced by this system has particularly high resolution in one axis with edge enhancement of certain features in the other axis. A practitioner skilled in the art could also employ radiation generation of distinct and separate energies with accompanying focusing optic geometries for multiple energy imaging. A practitioner skilled in the art could also thus employ radiation energies for preferential absorption, generally by additional contrast agent, and subsequent analysis via image subtraction routines.

Figure 5:
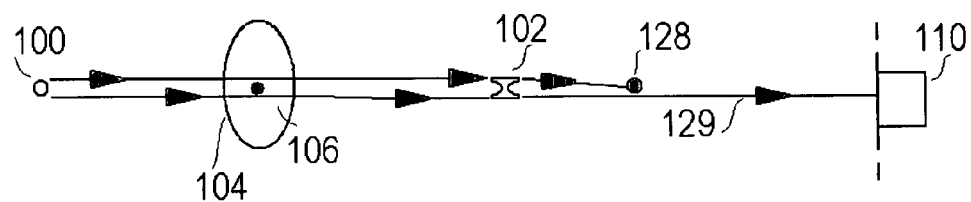
FIG. 5 is a diagrammatic plan top view of a schlieren radiography system in accordance with an embodiment of the invention, wherein phase and/or scattering content is enhanced by means of a stop to reduce absorption content.

A diagrammatic top view of a system for forming an image of an object in accordance with an embodiment of this invention is shown in FIG. 5. A radiation line origin with an axis of narrow spatial dimension 100 produces rays of high spatial purity. Some of these rays transmit through the object 104 and fall incident onto a two-dimensional focusing optic 102. The radiation focusing optic 102 is positioned to cast an image of the origin onto a stop or phase shifter 128, such that rays un-deviated by the refractive or scattering properties of the object will be partially or totally terminated or shifted in phase by the stop or phase shifter 128. Rays 129 deviated by the refractive or scattering properties of object 104, and particularly the boundary of components of differing density 106, will not encounter the stop or phase shifter and will be brought to focus on a detector 110.

Figure 6:
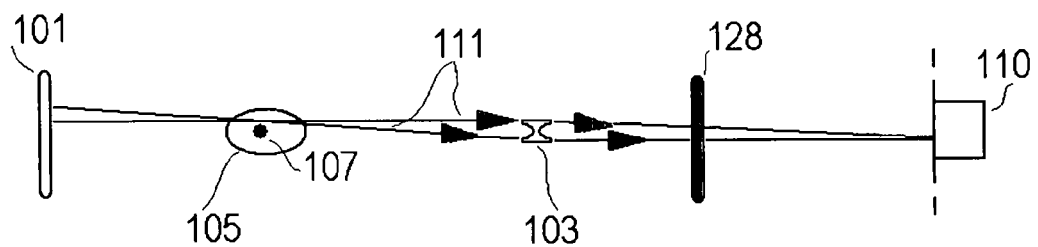
FIG. 6 is a diagrammatic plan side view of the system described in FIG. 5, wherein a one-dimensional radiation optic captures and focuses points of phase or scattering content within the object.

A diagrammatic side view of the same system is shown in FIG. 6. A radiation line origin with an axis of long spatial dimension 101 produces rays of low spatial purity. Rays deviated by the refractive or scattering properties of object 105, and particularly the boundary of components of differing density 107, will not encounter the stop or phase shifter and will be brought to focus on a detector 110. All such rays passing through points in the object and a two-dimensional focusing optic 103 will be focused onto the detector 110. A practitioner skilled in the art could also employ other radiation focusing optics to equal effect. A practitioner skilled in the art could also employ multiple line origins and multiple stops or phase shifters to increase effective field of view.

Figure 7:
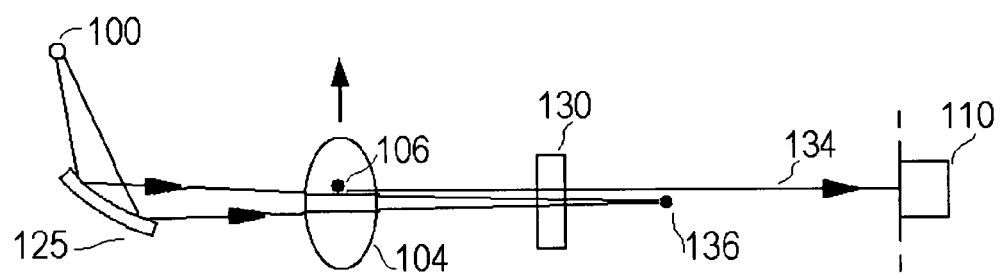
FIG. 7 is a diagrammatic plan top view of a schlieren radiography system in accordance with an embodiment of the invention, wherein enhanced phase and/or scattering content is represented in an enlarged field of view image.

A diagrammatic top view of a system for forming an image of an object in accordance with an embodiment of this invention is shown in FIG. 7. A radiation line origin with an axis of narrow spatial dimension 100 produces rays of high spatial purity. Some of these rays reflect from the surface of a curved crystal or curved multilayer mirror 125. Such an approach has each ray of a selected wavelength impinge on the crystal structure such to satisfy the correct Bragg condition and be reflected. All rays emitted from the radiation source that do not encounter the reflector at a correct angle, or are not of the correct wavelength, are not reflected. Monochromatic rays thus reflected are made to focus onto the narrow axis of a beam stop or phase shifter 136 placed beyond the region of the object 104. The curved crystal or curved multilayer mirror 125 is thus used to cast an one-dimensional image of the line origin onto the line-shaped stop or phase shifter 136, such that rays un-deviated by the refractive or scattering properties of the object will be partially or totally terminated by the stop or phase shifter 136. Rays 134 deviated by the refractive or scattering properties of object 104, and particularly the boundary of components of differing density 106, will not encounter the stop or phase shifter and will fall incident on a detector 110. A one-dimensional radiation imaging optic 130 will not have a focusing effect on such rays in this axis.

Figure 8:
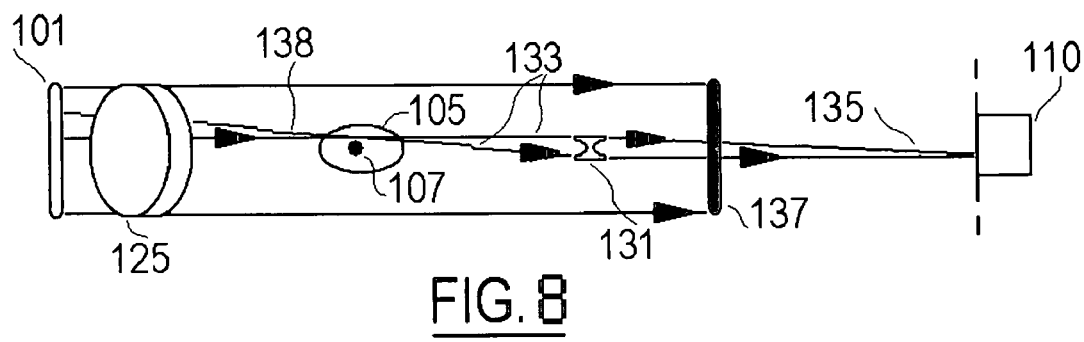
FIG. 8 is a diagrammatic plan side view of the system described in FIG. 7, wherein a one-dimensional radiation optic captures and focuses phase and/or scattering content in an enhanced field of view image.

A diagrammatic side view of the same system is shown in FIG. 8. A radiation line origin with an axis of long spatial dimension 101 produces rays of low spatial purity. Some of these rays reflect from the surface of a curved crystal or curved multilayer mirror 125. As described above, rays deviated by the refractive or scattering properties of object 105, and particularly the boundary of components of differing density 107, will not encounter the stop or phase shifter 137 and will encounter a detector 110. All such rays 133 passing through points in the object 105, and particularly the boundary of components of differing density 107, and a one-dimensional focusing optic 131 will be focused 135 onto the detector 110. This optical condition results in improved resolution as the long axis of radiation origin 101 provides rays 138 to backlight all features within the object 105. A practitioner skilled in the art could also employ other radiation focusing optics to equal effect of eliminating blur in the long axis of beam origin. A practitioner skilled in the art could also employ multiple line origins, multiple reflectors and multiple stops or phase shifters to increase effective field of view.

Figure 9:
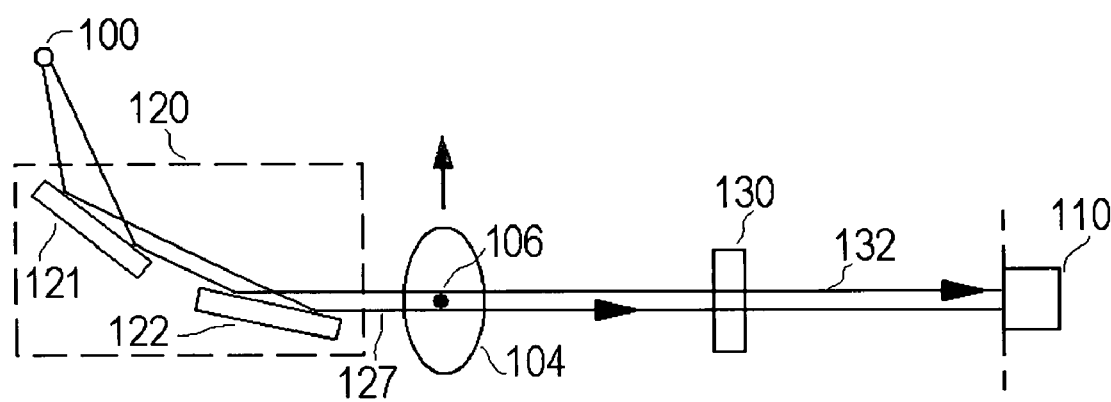
FIG. 9 is a diagrammatic plan top view of a schlieren radiography system in accordance with an embodiment of the invention, wherein minor phase and/or scattering content is represented in one axis of the image.

A diagrammatic top view of a system for forming an image of an object in accordance with an embodiment of this invention is shown in FIG. 9. A radiation line origin with an axis of narrow spatial dimension 100 produces rays of high spatial purity. Some of these rays reflect from the surfaces a double crystal monochromator 120. Asymmetrically-cut perfect crystals are used in series for such monochromators such that the reflected rays have spatial purity of nearly perfect lateral coherence in the diffraction plane, albeit at reduced intensity as the beam is also expanded. Rays thus reflected 127 are highly collimated in the narrow axis of the beam's line origin. Another way of stating this is to say that the waveform is planer in the diffraction axis. A one-dimensional radiation imaging optic 130 will not have a focusing effect in this axis on such rays.

Figure 10:
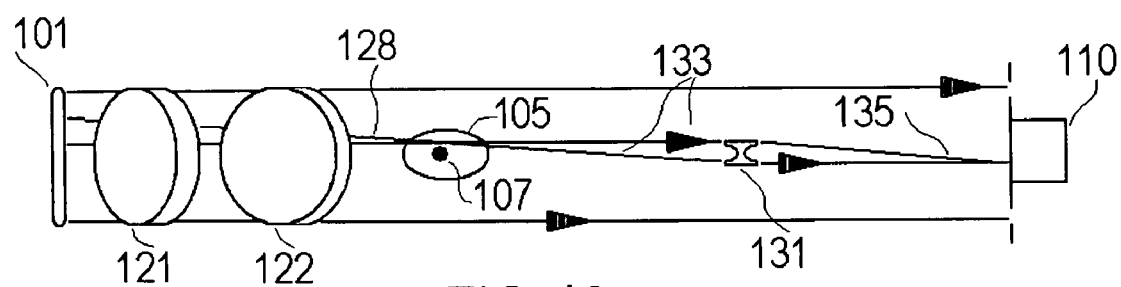
FIG. 10 is a diagrammatic plan side view of the system described in FIG. 9, wherein a one-dimensional radiation optic captures and focuses minor phase and/or scattering content within the object.

A diagrammatic side view of the same system is shown in FIG. 10. A radiation line origin with an axis of long spatial dimension 101 produces rays of low spatial purity. Some of these rays reflect from the surfaces of a first reflector 121 and a second reflector 122 as described above. In this axis, no improvement in beam quality is provided by the reflectors. As such, no rays in this axis are expected to interfere and produce contrast enhancement. Instead, all rays from points within the field of view including rays 133 emitted from boundaries of differing densities 107 within the object 105, will fill the aperture of the one-dimensional focusing optic 131 and be brought to focus 135 on a detector 110. A practitioner skilled in the art could also employ other radiation focusing optics to equal effect of eliminating blur in the long axis of beam origin. A practitioner skilled in the art could also employ scanning to produce full 2-D or 3-D image sets.

Figure 11:
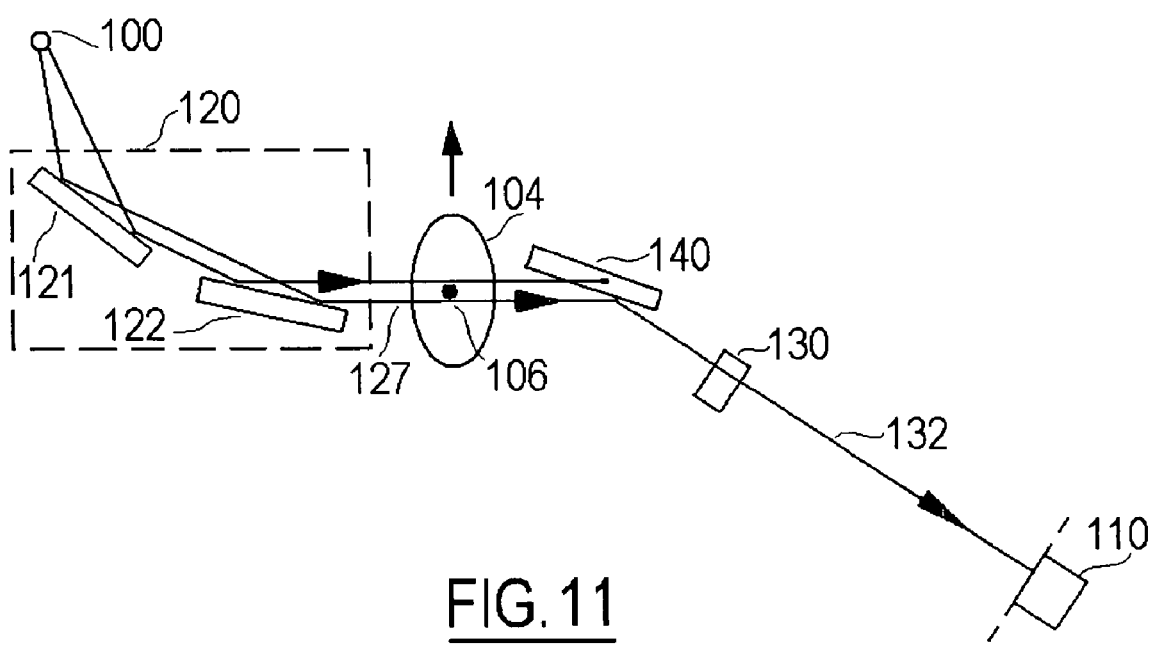
FIG. 11 is a diagrammatic plan top view of a schlieren radiography system in accordance with an embodiment of the invention, wherein a discriminating reflector to used to enhance very minor phase and/or scattering content in one axis of the image.

A diagrammatic top view of a system for forming an image of an object in accordance with an embodiment of this invention is shown in FIG. 11. A radiation line origin with an axis of narrow spatial dimension 100 produces rays of high spatial purity. Some of these rays reflect from the surfaces a double crystal monochromator 120. Rays thus reflected 127 are highly collimated in the narrow axis of the beam's line origin. Immediately following the object 104, is placed a structured multilayer reflector 140. The structure of the multilayers are aligned with and set to absorb the direct rays of the monochromator 120 in a type of Fabry-Perot interferometer. Rays 132 deviated by the refractive or scattering properties of object 104, and particularly the boundary of components of differing density 106, will reflect from the structured multilayer and fall incident on the detector 110. The resulting image is comprised almost exclusively of the boundary of differing densities 106 within the object 104. A one-dimensional radiation imaging optic 130 will not have a focusing effect on such rays in this axis.

Figure 12:
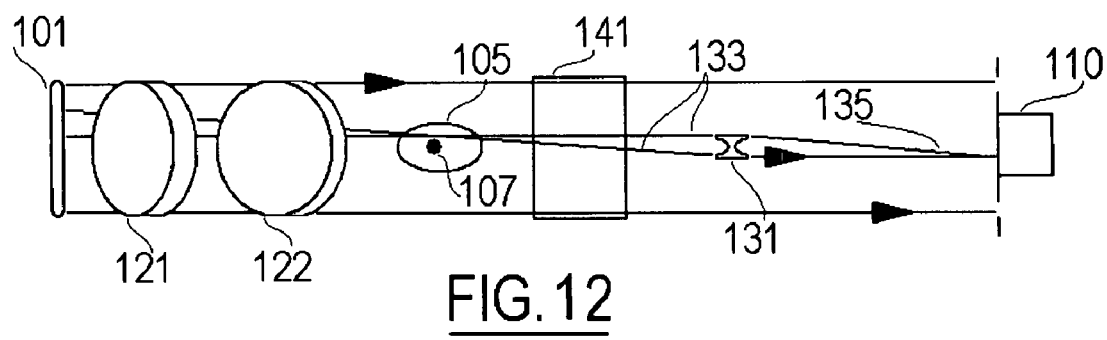
FIG. 12 is a diagrammatic plan side view of the system described in FIG. 11, wherein a one-dimensional radiation optic captures and focuses very minor phase and/or scattering content within the object.

A diagrammatic side view of the same system is shown in FIG. 12. A radiation line origin with an axis of long spatial dimension 101 produces rays of low spatial purity. Some of these rays reflect from the surfaces of a first reflector 121 and a second reflector 122 as described above. In this axis, no improvement in beam quality is provided by the reflectors. As such, no rays in this axis are expected to interfere and produce contrast enhancement. Instead, rays 133 emitted from boundaries of differing densities 107 within the object 105 will reflect off the structured multilayer 141 and fill the aperture of the one-dimensional focusing optic 131 and be brought to focus 135 on a detector 110. A practitioner skilled in the art could also employ other radiation focusing optics to equal effect of eliminating blur in the long axis of beam origin. A practitioner skilled in the art could also employ scanning to produce full 2-D or 3-D image sets.

Figure 13:
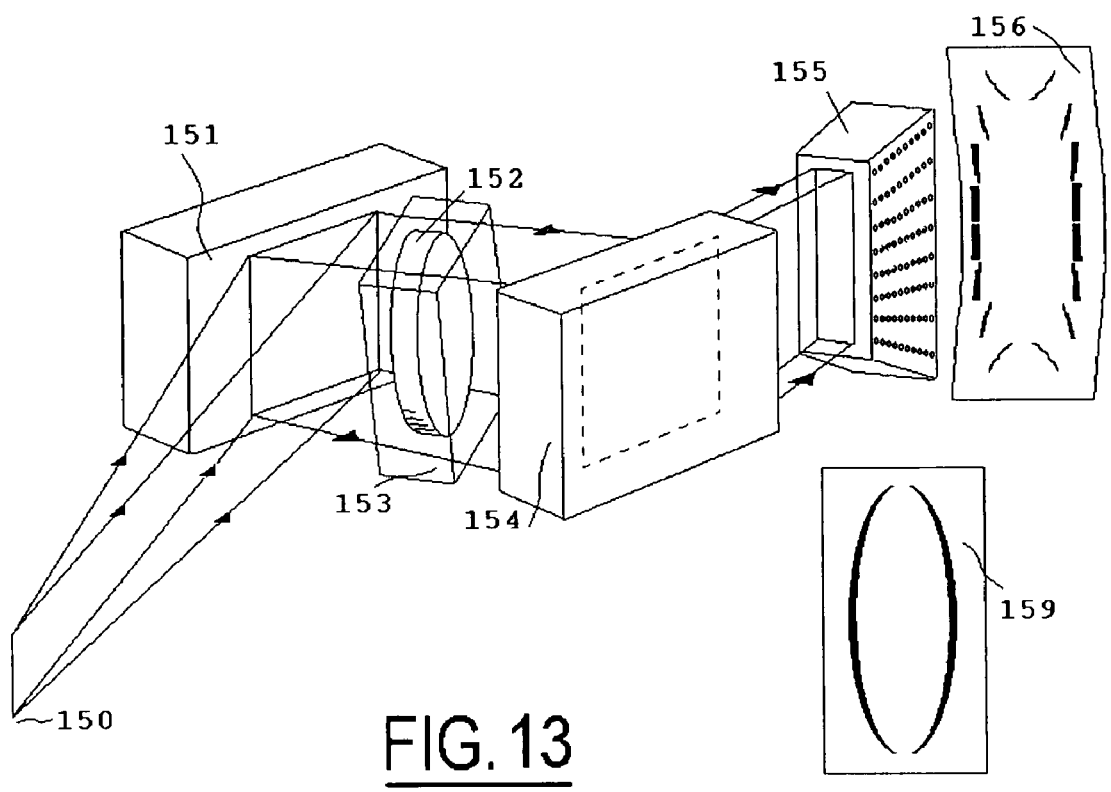
FIG. 13 is an isotropic diagram of the system described in FIG. 11 and FIG. 12, wherein an array of one-dimensional imaging optics capture a full field view of the phase and/or scattering content with a digitally rearranged display.

An isotropic diagram of the above described system employing an array of one-dimensional imaging optics is shown in FIG. 13. Radiation is projected from a line source of origin 150 onto an asymmetric crystal monochromator 151, whereby some of the incident rays are reflected with excellent lateral coherence in the axis of narrow origin. The radiation such produced transmits through an object of a certain density 153. Inside the object 153 is a component of a differing density 152. All direct, un-deviated rays emitted from the object 153 will be absorbed by the structured multilayer 154. Rays that undergo angular deviation at the boundary of the density change, which is the edge of the internal component 152, will be reflected from the structured multilayer 154. Rays thus reflected fall incident on an array of one dimensional radiation imaging optics 155. Each individual compound refractive lens in the array has only a limited field of view, and each lens images a separate portion of the object. Each point in such portion is effectively backlit by rays emitted by the long dimension of the line origin of radiation. The result is that the detector 156 captures a full view of the refractive properties of the object, albeit individual portions are inverted per the standard lens imaging effect. A conversion is performed electronically to stitch the image together in correct orientation 159. This system can also employ scanning to produce full 2-D or 3-D image sets.

An alternative system to the above described system employs a perfect crystal analyzer in direct replacement of the structured multilayer diagrammed in FIG. 11, 140, FIG. 12, 141, FIG. 13, 154. The system would adjust the angle incident on the crystal analyzer to capture images with varying content of refractive and scattering properties. Generally, the crystal alignments use the sides of the crystal's angular reflection (rocking) curve to halve the intensity of the un-deviated rays from the monochromator. A practitioner skilled in the art could capture multiple images from such angular alignment variation and combine these images in ways to isolate certain refraction, scattering, and absorption features of the object. Again, rays that undergo angular deviation at the boundary of the density change, which is the edge of the internal components will be reflected from the crystal analyzer in proportion to the crystal's angular alignment. Rays thus reflected fall incident on one or an array of one dimensional radiation imaging optics. Each individual optic has only a limited field of view and images a separate portion of the object. Each point in such portion is effectively backlit by rays emitted by the long dimension of the line origin of radiation. The result is that the detector captures a full view of the refractive and/or scattering properties of the object, albeit individual portions are inverted per the standard lens imaging effect. A conversion is performed electronically to stitch the image together in correct orientation. This system can also employ scanning to produce full 2-D or 3-D image sets.

Figure 14:
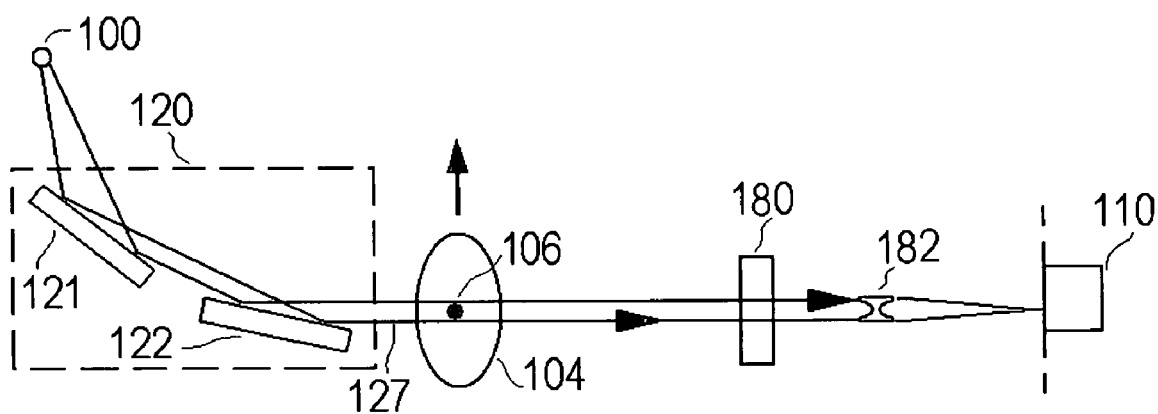
FIG. 14 is a diagrammatic plan top view of a sensor in accordance with an embodiment of the invention, wherein radiation optics are used to measure perturbed waveform sections with results used to reconstruct a schlieren image of object.

A diagrammatic top view of a sensor for analyzing an object in accordance with an embodiment of this invention is shown in FIG. 14. A radiation line origin with an axis of narrow spatial dimension 100 produces rays of high spatial purity. Some of these rays reflect from the surfaces of a double crystal monochromator 120. For use in this invention, the first reflector 121 is in series with the second reflector 122, such that the incident beam is greatly expanded with an accompanying improvement in transverse coherence. Rays thus reflected 127 are highly collimated in the narrow axis of the beam's line origin. A one-dimensional radiation optic 182 is used to focus the collimated beam to a few rows of pixels on the detector 110. These are called reference pixels, and are here presented as horizontal rows. Rays deviated by the refractive properties of object 104, and particularly the boundary of components of differing density 106, will move accompanying portions of the focused beam vertically from the reference pixels to fall on nearby pixels. The change in position of the focused beam is a record of the distortion of the radiation waveform. Analysis of this information results in a reconstruction of the object's refractive features. Another one-dimensional radiation imaging optic 180 will not have a focusing effect on rays in this axis.

Figure 15:
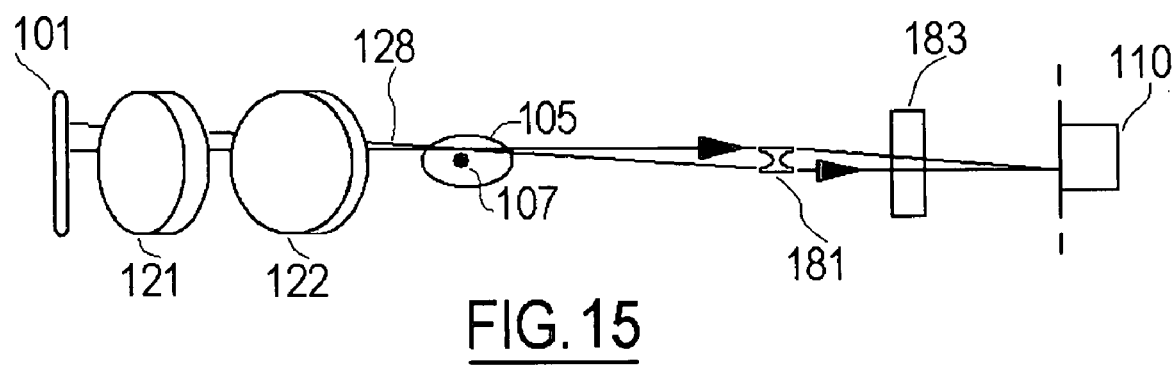
FIG. 15 is a diagrammatic plan side view of the sensor described in FIG. 14, wherein crossed one-dimensional radiation optics record waveform angular displacements.

A diagrammatic side view of the same sensor is shown in FIG. 15. A radiation line origin with an axis of long spatial dimension 101 produces rays of low spatial purity. Some of these rays reflect from the surfaces of a first reflector 121 and a second reflector 122 as described above. In this axis, no improvement in beam quality is provided by the reflectors. Rays emitted from any point in the object 105 will fill the aperture of the one-dimensional focusing optic 181 and be brought to focus on a detector 110. Consequently, rays within the field of view of the radiation focusing optic 181 that transmit through a point in the object 105 will be collected and focused to a pixel on the detector 110. This optical condition results in improved resolution as the long axis of radiation origin 101 backlights 128 all features within the object 105. The other one-dimensional radiation imaging optic 183, discussed above and here shown in side view, will not have a focusing effect on rays in this axis.

The above described sensor as diagrammed in FIG. 14 and FIG. 15 is a complex optical system, with designed-in astigmatism. It uses crossed one dimensional radiation optics, each with different focal lengths. Information from the sensor is used to derive an image of the object's refractive properties, typically using Shack Hartmann analysis—commonly used for optical wavefront distortion analysis. This embodiment of the invention uses penetrating radiation with good lateral coherence in one axis, analyzes the distorted waveform of collimated rays transiting an object, and derives an image of the object's phase properties in one axis. Scanning will produce full 2-D sets of data for a large object. An array of one-dimensional radiation optics crossed at ninety degrees with another array of one-dimensional radiation optics significantly reduces the need for macro-scanning, but allows for micro-scanning to improve resolution by use of calculated spot centroids. Crossed arrays use a single set of reference pixels isolated for each single set of crossed radiation optics.

Another sensor for analyzing an object in accordance with an embodiment of this invention uses a radiation beam of good lateral coherence in both axes. A two-dimensional radiation optic is used to focus the collimated beam to a few reference pixels on the detector. Rays deviated by the refractive properties of the object placed in the collimated beam, and particularly the boundary of components of differing density, will move the focused beam from the reference position such that they fall incident on nearby pixels. The change in position of the focused beam is a record of the distortion of the radiation waveform, averaged across the aperture of the optic. Analysis of this information results in a reconstruction of the object's refractive features in both axes. An array of nearly identical two-dimensional radiation optics significantly reduces the need for macro-scanning, but allows for micro-scanning to improve resolution by use of spot centroids. A single set of reference pixels are isolated for each single two-dimensional radiation optic.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

Portions of the present detailed discussion have been for the case of x-rays. As is well understood by those skilled in the art, similar classes of optical devices and configurations suited to neutron imaging are possible, making proper allowance for the different theory for scattering of neutrons and the differences in magnitudes and signs of the deviations of the refractive indices of neutrons from unity for different materials.

What is claimed is:

1. A system for forming an image of an object, said image including internal features of said object, said system comprising:
    means for generating a penetrating radiation beam;
    said means for generating having one or more line origin(s) for generating said beam providing that said beam has high spatial purity along a narrow axis of said beam origin(s) and low spatial purity along a long axis of said beam origin(s);
    a radiation imaging optic;
    means for supporting said object to provide that said beam is directed through said object and through said radiation imaging optic;
    said radiation imaging optic arranged to form at least a partial image of said object presented on a detector screen;

said partial image including at least one of phase and scattering content of said object's internal features in a direction along one axis of said beam.

2. The system of claim 1 wherein said radiation imaging optic is arranged to collect and focus said partial image in two dimensions.

3. The system of claim 1 wherein said radiation imaging optic is arranged to collect and focus said partial image in one dimension with an axis of ray collection and focusing aligned with a long dimension of said line origin of radiation beam.

4. The system of claim 2 comprising:
a far field detector;
one of a stop and phase shift filter;
said radiation image optic arranged to focus an image of said line radiation origin exactly upon said one of a stop and phase shifter and permit another image of said object to be focused on said far field detector; and
said another image of said object comprising rays deviated by refraction and/or scattering properties of said object's internal features.

5. The system of claim 3 wherein said radiation image optic comprises crystals being one of:
A.) bent monochromator crystals;
B.) curved multilayer synthetic crystals;
for diffracting said radiation beam providing that an image of said line origin is focused exactly on one of:
A.) a stop;
B.) a phase shifter
providing that said image focused at a far field detector comprises rays deviated by said internal features of said object.

6. The system of claim 3 wherein:
said means for generating a radiation beam generates a beam having one part and another part;
said one part generated by one transmission energy; and focused onto a detector by said radiation imaging optic at a particular focal distance from said object;
said another part generated by another transmission energy and focused onto a detector by said radiation imaging optic at a different focal distance from said object; and
wherein at least two images are detected, each for different transmitted energies, and a phase and/or absorption image is derived from an analysis of the two detected images.

7. The system of claim 6 wherein said image analysis is arranged to derive said phase responsive image separate from said absorption image for separate analysis of chemical elemental dependent features, such as from contrast media, of said object.

8. A system for displaying an image of at least one phase related and absorption related features of an object, said system comprising;
line origin means for projecting a radiation beam;
monochromator crystals arranged for diffracting said radiation beam in the narrow axis of said line origin;
means for supporting said object to permit transmitting said beam through said object;
a radiation imaging optic;
means for generating an image from said image signal and enabling a viewer to analyze said image for phase and absorption related features in one axis of said object.

9. A system for displaying an image of at least one phase related and absorption related features of an object, said system comprising;
line origin means for projecting a radiation beam;
monochromator crystals arranged for diffracting said radiation beam in the narrow axis of said line origin;
means for supporting said object to permit transmitting said beam through said object;
a structured multilayer analyzer arranged to receive a portion of said transmitted beam at an angle of incidence whereby all rays not deviated by features of the object are not allowed to reflect;
a radiation imaging optic;
means for transmitting said portion of said beam from said structured multilayer analyzer through said radiation imaging optic; to generate an image signal;
means for generating an image from said image signal and enabling a viewer to analyze said image for phase and scattering related features in said object, with absorption related features suppressed.

10. A system for displaying an image of at least one phase related and absorption related features of an object, said system comprising;
line origin means for projecting a radiation beam;
monochromator crystals arranged for diffracting said radiation beam;
means for supporting said object to permit transmitting said beam through said object;
a crystal analyzer arranged to receive a portion of said transmitted beam at an angle of incidence;
a radiation imaging optic;
means for transmitting said portion of said beam from said crystal analyzer through said radiation imaging optic; to generate an image signal;
means for generating an image from said image signal and enabling a viewer to analyze said image for phase and absorption related features in said object.

11. The system of claim 10 wherein said crystal analyzer is a Bragg analyzer.

12. The system of claim 10 wherein said crystal analyzer is a Laue analyzer.

13. The system of claim 10 wherein said radiation imaging system comprises:
means for generating a first image signal from a portion of said beam emitted at a first angular position relative to said crystal analyzer;
means for generating a second image signal from a portion of said beam emitted at a second angular position relative to said crystal analyzer;
means for combining said first and second image signals to generate a combined image signal;
means for generating a combined image from said combined image signal having phase and scattering content on one axis.

14. The system of claim 10 wherein said first and second angular positions are within a rocking curve of said crystal analyzer.

15. The system of claim 10 wherein said first angular position is a low rocking angle setting and said second angular position is a high rocking angle setting of said crystal analyzer.

16. The system of claim 10 wherein said first and second image signals are digital.

17. The system of claim 10 wherein said combined image is a digital combined signal from which is generated a combined image enhanced by said at least one of phase related and absorption related features of said object.

18. A system for deriving an image of at least one phase related feature of an object, said system comprising;
A first array of near identical radiation one-dimensional focusing optics, and a second array of near identical radiation one-dimensional focusing optics set at ninety degrees to said first array;

said first array of radiation one-dimensional focusing optics aligned parallel to the long axis of beam origin;

said first array of radiation one-dimensional focusing optics positioned such that the detector is at a distance exactly the equal the focal length of radiation one-dimensional focusing optics;

said detector having a greater number of resolution elements than the total number of radiation one-dimensional focusing optics in said first array;

said resolution elements being segregated to detect a line focus of radiation from only one radiation focusing optic in said first array;

said resolution elements measuring the effect of radiation beam phase change generated by said refractive properties of said internal features of said object by associated change in position of portions of said line focus of radiation;

said second array of near identical radiation one-dimensional focusing optics aligned perpendicular to the long axis of beam origin;

said second array of radiation one-dimensional focusing optics positioned such that the detector is at a distance such that an image of the object is produced in one line on the detector, with individual segments of said line capturing transmitted radiation from individual portions of said object;

a calculation performed on said measured effects determining the distortion of the radiation wavefront;

an image of one axis of object's internal refraction properties being derived from a Shack-Hartmann analysis of said distorted radiation wavefront.

19. The system of claim 18 wherein the system for deriving an image of at least one phase related feature of an object comprises;

short line origin (near-point) means for projecting a radiation beam;

monochromator crystals arranged for diffracting said radiation beam in one axis;

means for supporting said object to permit transmitting said beam through said object;

an array of near identical radiation two-dimensional focusing optics;

said array of radiation two-dimensional focusing optics positioned such that the detector is at a distance exactly the equal the focal length of radiation two-dimensional focusing optics;

said detector having a greater number of resolution elements than the total number of radiation two-dimensional focusing optics in said array;

said resolution elements being segregated to detect a point focus of radiation from only one radiation two-dimensional focusing optic in said array;

said resolution elements measuring the effect of radiation beam phase change generated by said refractive properties of said internal features of said object by associated change in position of said point focus of radiation;

a calculation performed on said measured effects determining the distortion of the radiation wavefront;

an image of both axes of object's internal refraction properties being derived from a Shack-Hartmann analysis of said distorted radiation wavefront.

* * * * *